(12) United States Patent
Reiley

(10) Patent No.: US 8,308,779 B2
(45) Date of Patent: Nov. 13, 2012

(54) SYSTEMS AND METHODS FOR THE FIXATION OR FUSION OF BONE

(75) Inventor: Mark A. Reiley, Washington, DC (US)

(73) Assignee: Si-Bone, Inc., San Jose, CA (US)

( * ) Notice: Subject to any disclaimer, the term of this patent is extended or adjusted under 35 U.S.C. 154(b) by 901 days.

(21) Appl. No.: 12/072,153

(22) Filed: Feb. 25, 2008

(65) Prior Publication Data

US 2008/0154316 A1    Jun. 26, 2008

Related U.S. Application Data

(62) Division of application No. 10/914,629, filed on Aug. 9, 2004, now abandoned.

(51) Int. Cl.
*A61B 17/04*     (2006.01)

(52) U.S. Cl. ........................ 606/300

(58) Field of Classification Search .......... 606/62–64, 606/300–321; 623/20.35–20.36, 23.15, 23.27; 411/439, 487–499, 511, 525–529
See application file for complete search history.

(56) References Cited

U.S. PATENT DOCUMENTS

| | | |
|---|---|---|
| 3,076,453 A | 2/1963 | Tronzo |
| 4,344,190 A | 8/1982 | Lee et al. |
| 4,501,269 A | 2/1985 | Bagby |
| 4,569,338 A | 2/1986 | Edwards |
| 4,612,918 A | 9/1986 | Slocum |
| 4,657,550 A | 4/1987 | Daher |
| 4,773,402 A | 9/1988 | Asher et al. |
| 4,834,757 A | 5/1989 | Brantigan |
| 4,961,740 A | 10/1990 | Ray et al. |
| 5,034,011 A | 7/1991 | Howland |
| 5,035,697 A | 7/1991 | Frigg |
| 5,102,414 A | 4/1992 | Kirsch |
| 5,108,397 A | 4/1992 | White |
| 5,122,141 A * | 6/1992 | Simpson et al. ............... 606/62 |
| 5,139,498 A | 8/1992 | Astudillo Ley |
| 5,147,367 A | 9/1992 | Ellis |
| 5,147,402 A | 9/1992 | Bohler et al. |
| 5,242,444 A | 9/1993 | MacMillan |
| 5,298,254 A | 3/1994 | Prewett et al. |
| 5,334,205 A | 8/1994 | Cain |
| 5,480,402 A * | 1/1996 | Kim ............................ 606/64 |
| 5,569,249 A | 10/1996 | James et al. |
| 5,593,409 A | 1/1997 | Michelson |
| 5,609,636 A | 3/1997 | Kohrs et al. |
| 5,626,616 A | 5/1997 | Speece |

(Continued)

FOREIGN PATENT DOCUMENTS

EP    1287796 A1    3/2003

(Continued)

OTHER PUBLICATIONS

PCT/US08/00202 ISR.

(Continued)

*Primary Examiner* — Thomas Barrett
*Assistant Examiner* — Melissa A Golob
(74) *Attorney, Agent, or Firm* — Shay Glenn, LLP

(57) ABSTRACT

A stem-like bone fixation device allows for bony in-growth on its surface and across fracture fragments or between bones that are to be fused.

20 Claims, 5 Drawing Sheets

U.S. PATENT DOCUMENTS

| | | | |
|---|---|---|---|
| 5,645,599 A | 7/1997 | Samani |
| 5,667,510 A | 9/1997 | Combs |
| 5,669,909 A | 9/1997 | Zdeblick et al. |
| 5,672,178 A | 9/1997 | Petersen |
| 5,713,904 A | 2/1998 | Errico et al. |
| 5,868,749 A | 2/1999 | Reed |
| 5,928,239 A | 7/1999 | Mirza |
| 5,968,047 A | 10/1999 | Reed |
| 6,010,507 A | 1/2000 | Rudloff |
| 6,053,916 A | 4/2000 | Moore |
| 6,096,080 A | 8/2000 | Nicholson et al. |
| 6,210,442 B1 | 4/2001 | Wing et al. |
| 6,214,049 B1 | 4/2001 | Gayer et al. |
| 6,221,074 B1 * | 4/2001 | Cole et al. .................. 606/62 |
| 6,241,732 B1 | 6/2001 | Overaker et al. |
| 6,270,528 B1 | 8/2001 | McKay |
| 6,302,885 B1 | 10/2001 | Essiger |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,565,566 B1 | 5/2003 | Wagner et al. |
| 6,582,431 B1 | 6/2003 | Ray |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,635,059 B2 | 10/2003 | Randall et al. |
| 6,666,868 B2 | 12/2003 | Fallin |
| 6,669,529 B1 | 12/2003 | Scaries |
| 6,723,099 B1 | 4/2004 | Goshert |
| 6,743,257 B2 | 6/2004 | Castro |
| 7,223,269 B2 | 5/2007 | Chappuis |
| 7,335,205 B2 | 2/2008 | Aeschlimann et al. |
| 7,481,831 B2 | 1/2009 | Bonutti |
| 7,648,509 B2 | 1/2010 | Stark |
| 7,922,765 B2 | 4/2011 | Reiley |
| 2001/0049529 A1 | 12/2001 | Cachia et al. |
| 2002/0049497 A1 | 4/2002 | Mason |
| 2002/0120275 A1 * | 8/2002 | Schmieding et al. ......... 606/104 |
| 2002/0128652 A1 | 9/2002 | Ferree |
| 2002/0143335 A1 | 10/2002 | von Hoffmann et al. |
| 2002/0151903 A1 | 10/2002 | Takei et al. |
| 2002/0183858 A1 | 12/2002 | Contiliano et al. |
| 2002/0198527 A1 | 12/2002 | Mückter |
| 2003/0032961 A1 | 2/2003 | Pelo et al. |
| 2003/0065332 A1 | 4/2003 | TenHuisen et al. |
| 2003/0233147 A1 | 12/2003 | Nicholson et al. |
| 2004/0024458 A1 | 2/2004 | Senegas et al. |
| 2004/0073216 A1 | 4/2004 | Lieberman |
| 2004/0073314 A1 | 4/2004 | White et al. |
| 2004/0087948 A1 | 5/2004 | Suddaby |
| 2004/0106925 A1 | 6/2004 | Culbert |
| 2004/0117022 A1 | 6/2004 | Marnay et al. |
| 2004/0147929 A1 | 7/2004 | Biedermann et al. |
| 2004/0181282 A1 | 9/2004 | Zucherman et al. |
| 2004/0225360 A1 | 11/2004 | Malone |
| 2005/0033435 A1 | 2/2005 | Belliard et al. |
| 2005/0107878 A1 | 5/2005 | Conchy |
| 2005/0124993 A1 | 6/2005 | Chappuis |
| 2005/0159749 A1 | 7/2005 | Levy et al. |
| 2005/0165398 A1 | 7/2005 | Reiley |
| 2005/0228384 A1 | 10/2005 | Zucherman et al. |
| 2005/0246021 A1 | 11/2005 | Ringeisen et al. |
| 2006/0036251 A1 | 2/2006 | Reiley |
| 2006/0129247 A1 | 6/2006 | Brown et al. |
| 2006/0293662 A1 | 12/2006 | Boyer et al. |
| 2007/0083265 A1 | 4/2007 | Malone |
| 2007/0149976 A1 | 6/2007 | Hale et al. |
| 2007/0156241 A1 | 7/2007 | Reiley et al. |
| 2008/0065215 A1 | 3/2008 | Reiley |
| 2009/0259261 A1 | 10/2009 | Reiley |
| 2010/0191292 A1 | 7/2010 | DeMeo et al. |
| 2010/0292738 A1 | 11/2010 | Reiley |
| 2011/0087294 A1 | 4/2011 | Reiley |
| 2011/0087296 A1 | 4/2011 | Reiley et al. |
| 2011/0118785 A1 | 5/2011 | Reiley |
| 2011/0118790 A1 | 5/2011 | Reiley |
| 2011/0118796 A1 | 5/2011 | Reiley et al. |
| 2011/0118841 A1 | 5/2011 | Reiley |
| 2011/0125268 A1 | 5/2011 | Reiley |

FOREIGN PATENT DOCUMENTS

| | | |
|---|---|---|
| JP | 05-176942 A | 7/1993 |
| WO | WO02/38054 | 5/2002 |
| WO | WO2004/002344 | 1/2004 |
| WO | WO2006003316 | 1/2006 |

OTHER PUBLICATIONS

Reiley, Mark A.; U.S. Appl. No. 13/078,530 entitled "Systems and methods for the fixation or fusion of bone," filed Apr. 1, 2011.

Reiley, Mark A.; U.S. Appl. No. 12/357,483 entitled "Systems and methods for the fixation or fusion of bone in the hand and wrist," filed Jan. 22, 2009 (abandoned).

* cited by examiner

SYSTEMS AND METHODS FOR THE FIXATION OR FUSION OF BONE

RELATED APPLICATIONS

This application is a divisional of co-pending U.S. patent application Ser. No. 10/914,629, filed Aug. 9, 2004, and entitled "Systems and Methods for Fixation or Fusion of Bone," which is incorporated herein by reference.

FIELD OF THE INVENTION

This application relates generally to the fixation of bone.

BACKGROUND OF THE INVENTION

Many types of hardware are available both for fracture fixation and for the fixation of bones that are to fused (arthrodesed).

Metal and absorbable screws are routinely used to fixate bone fractures and osteotomies. It is important to the successful outcome of the procedure that the screw is able to generate the compressive forces helpful in promoting bone healing.

SUMMARY OF THE INVENTION

The invention provides bone fixation devices and related methods for stabilizing bone segments. The systems and methods include a stem-like structure adapted for passage between adjacent bone segments. At least a portion of the stem-like structure includes a surface that enhances bony in-growth. Boney in-growth into the stem-like structure helps speed up the fusion process or fracture healing time.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

Figure 1:
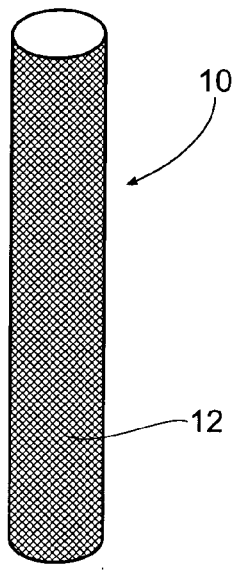
FIG. 1 is a perspective view of a bone fixation stem having a boney in-growth surface of a mesh configuration.

FIG. 1 shows a device 10 sized and configured for the fixation of bone fractures or for the fixation of bones which are to be fused (arthrodesed). The device 10 comprises an elongated, stem-like structure. The device 10 can be formed—e.g., by machining, molding, or extrusion—from a material usable in the prosthetic arts, including, but not limited to, titanium, titanium alloys, tantalum, chrome cobalt, surgical steel, or any other total joint replacement metal and/ or ceramic, sintered glass, artificial bone, any uncemented metal or ceramic surface, or a combination thereof. Alternatively, the device 10 may be formed from a suitable durable biologic material or a combination of metal and biologic material, such as a biocompatible bone-filling material. The device 10 may be molded from a flowable biologic material, e.g., acrylic bone cement, that is cured, e.g., by UV light, to a non-flowable or solid material.

The device 10 can take various shapes and have various cross-sectional geometries. The device 10 can have, e.g., a generally curvilinear (i.e., round or oval) cross-section, or a generally rectilinear cross section (i.e., square or rectangular), or combinations thereof. As will be described in greater detail later, the device 10 can be conical or wedge shaped.

The structure 10 includes surface texturing 12 along at least a portion of its length to promote bony in-growth on its surface. The surface texturing 12 can comprise, e.g., through holes, and/or various surface patterns, and/or various surface textures, and/or pores, or combinations thereof. The device 10 can be coated or wrapped or surfaced treated to provide the surface texturing 12, or it can be formed from a material that itself inherently possesses a surface conducing to bony in-growth, such as a porous mesh, hydroxyapetite, or other porous surface. The device 10 may further be covered with various other coatings such as antimicrobial, antithrombotic, and osteoinductive agents, or a combination thereof. The surface texturing 12 may be impregnated with such agents, if desired.

Figure 2:
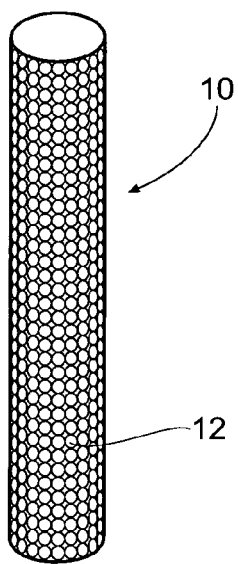
FIG. 2 is a perspective view of an alternative embodiment of a bone fixation stem having a boney in-growth surface of a beaded configuration.
Figure 3:
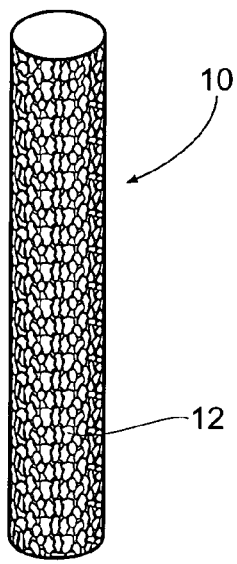
FIG. 3 is a perspective view of an alternative embodiment of a bone fixation stem having a boney in-growth surface of a trabecular configuration.

The configuration of the surface texturing 12 can, of course, vary. By way of examples, FIG. 1 shows the surface 12 as an open mesh configuration; FIG. 2 shows the surface 12 as beaded configuration; and FIG. 3 shows the surface 12 as a trabecular configuration. Any configuration conducive to bony in-growth will suffice.

Figure 4:
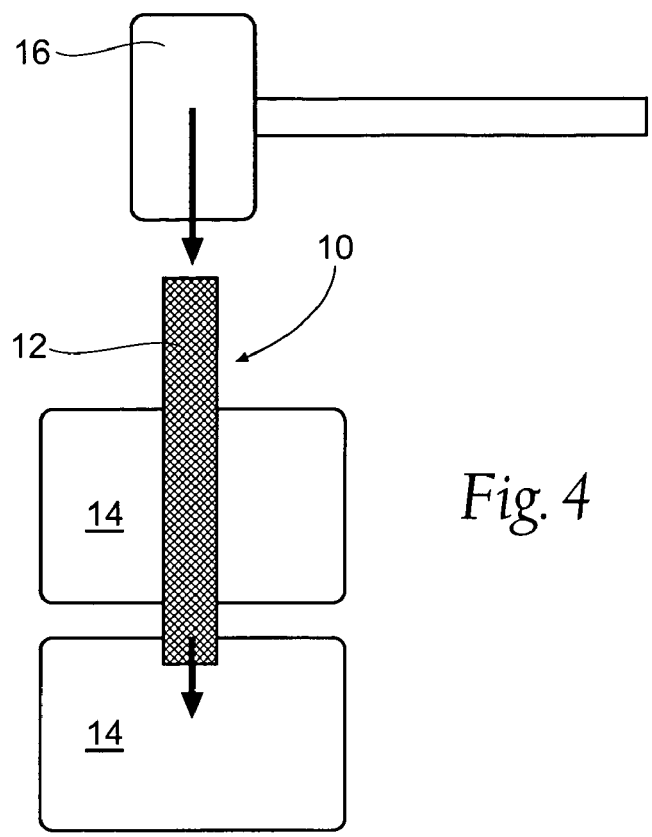
FIG. 4 is a schematic view of a bone fixation stem of the type shown in Fig. being inserted into bone across a fracture line or bone joint.

In use (see FIGS. 4 and 5), the device 10 is inserted into a space between two adjacent bone surfaces, e.g., into a fracture site or between two bones (e.g., adjacent vertebral bodies) which are to be fused together. In FIG. 4, the device 10 is shown being tapped into bone through bone segments 14 (i.e., across a fracture line or between adjacent bones to be fused) with a tap 16. The bone may be drilled first to facilitate insertion of the device 10. The bony in-growth surface 12 along the surface of the device 10 accelerates bony in-growth into the device 10. Boney in-growth into the device 10 helps speed up the fusion process or fracture healing time.

Figure 5:
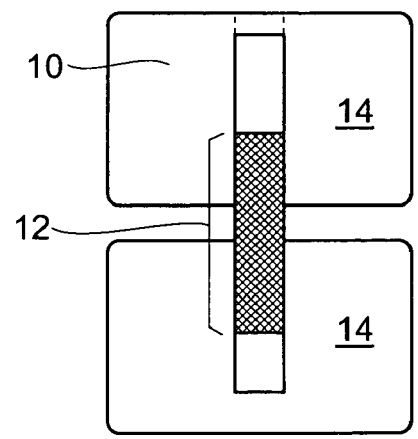
FIG. 5 is a schematic view of a bone fixation stem positioned within bone and illustrating a boney in-growth surface of the stem extending across a fracture line or bone joint.

The bony in-growth surface 12 may cover the entire outer surface of the device 10, as shown in FIG. 4, or the bony in-growth surface 12 may cover just a specified distance on either side of the joint surface or fracture line, as shown in FIG. 5.

The size and configuration of the device 10 can be varied to accommodate the type and location of the bone to be treated as well as individual anatomy.

Figure 6:
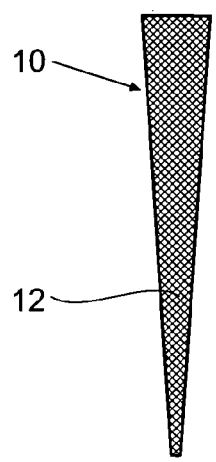
FIG. 6 is a front plan view of an alternative embodiment of a bone fixation stem having a boney in-growth surface in which the stem has a conical configuration.
Figure 7:
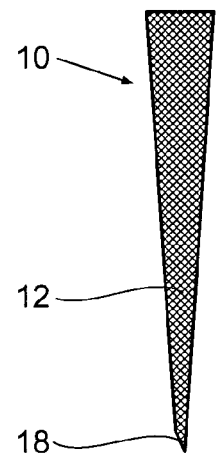
FIG. 7 is front plan view of an alternative embodiment of a bone fixation stem having a boney in-growth surface in which the stem has a beveled distal tip.
Figure 8A:
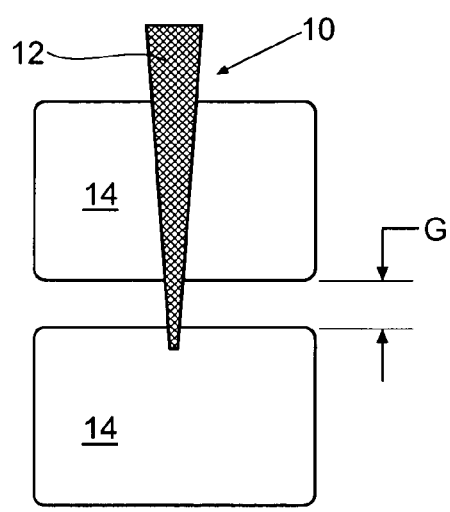
FIGS. 8A and 8B are schematics illustrating the insertion of a conical bone fixation stem of the type shown in FIG. 6 to reduce the gap between bone segments.
Figure 8B:
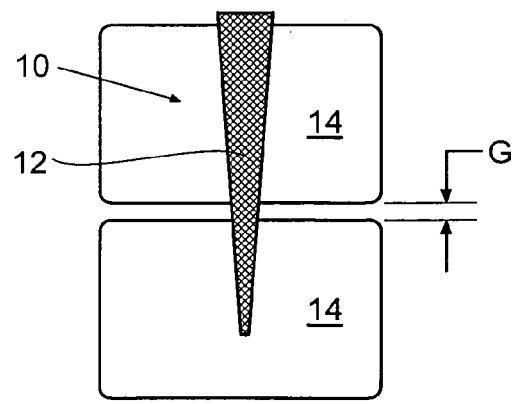

As FIG. 6 shows, the device 10 can be angled or tapered in a conical configuration. The degree of angle can be varied to accommodate specific needs or individual anatomy. A lesser degree of angle (i.e., a more acute angle) decreases the risk of splitting the bone as the device 10 is tapped into the bone or the fracture segments 14. The device 10 may also include a beveled distal tip 18 to further add in insertion of the device 10 into bone, as shown in FIG. 7. As shown in FIGS. 8A and 8B, the conical shape also helps drive the joint surfaces or fracture fragments together, reducing the gap (G) between the bone segments 14.

In FIGS. 9 to 12, the device 10 is cannulated, having a central lumen or throughbore 20 extending through it, to assist in the placement of the device 10 within bone.

Figure 9:
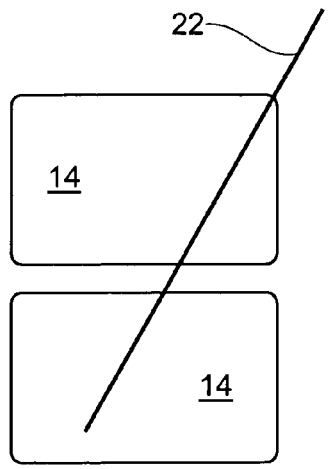
FIG. 9 is a schematic illustrating a guidewire being introduced into bone across bone segments.
Figure 10:
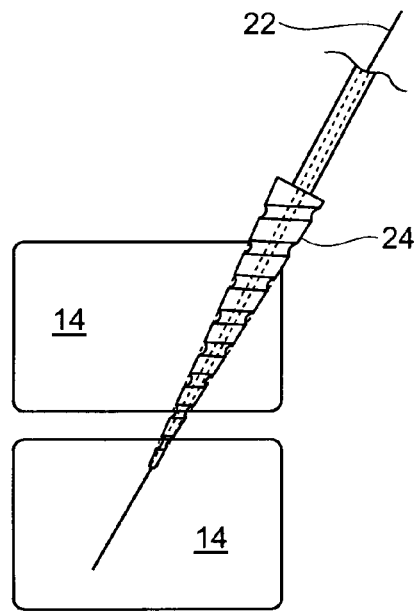
FIG. 10 is a schematic similar to FIG. 9 and illustrating a drill bit being introduced over the guidewire.
Figure 11:
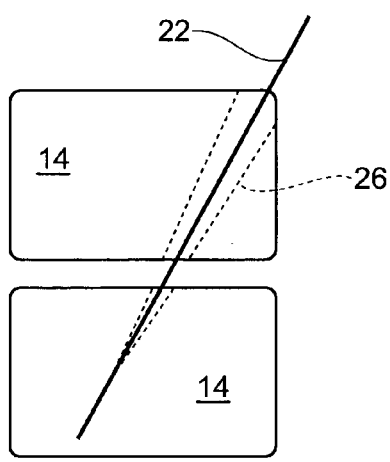
FIG. 11 is a schematic similar to FIG. 10 and illustrating a bore formed in the bone remaining after withdrawal of the drill bit.
Figure 12:
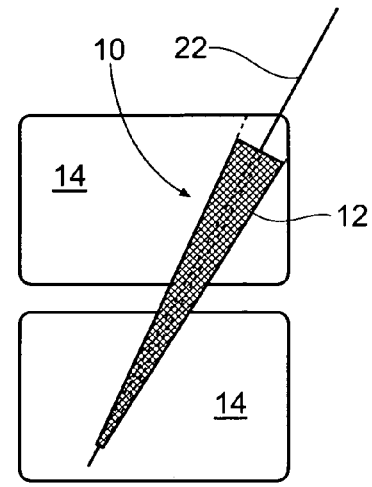
FIG. 12 is a schematic similar to FIG. 11 and illustrating insertion of a bone fixation stem into the pre-formed bore.

In use, the physician can insert a conventional guide pin 22 through the bone segments 14 by conventional methods, as FIG. 9 shows. A cannulated drill bit 24 can then be introduced over the guide pin 22, as seen in FIG. 10. A single or multiple drill bits 24 can be employed to drill through bone fragments or bone surfaces to create a bore 26 of the desired size and configuration. In the illustrated embodiment, the drill bit 24 is sized and configured to create a conical bore 26 similar in size and configuration to the device 10. The bore 26 is desirably sized and configured to permit tight engagement of the device 10 within the bore 26 and thereby restrict movement of the device 10 within the bore 26. The pre-formed bore 26 may be slightly smaller than the device 10, while still allowing the device 10 to be secured into position within the bore 26 by tapping. As seen in FIG. 11, the drill bit 24 is then withdrawn. The device 10 is then inserted into the bore 26 over the guide pin 22, as FIG. 12 shows. The guide pin 22 is then withdrawn.

Alternatively, the device 10 itself can include screw-like threads along the body for screwing the device into place. In the arrangement, the device 10 can be self-tapping. Also in this arrangement, the device 10 can be cannulated for use with a guide pin 22, or it need not be cannulated.

Multiple devices 10 may be employed to provide additional stabilization. While the use of multiple devices 10 will now be described illustrating the use of multiple devices 10 of the same size and configuration, it is contemplated that the devices 10 may also be of different size and/or configuration, e.g., one device 10 is of a cylindrical configuration and a second device 10 is of a conical configuration.

Figure 13:
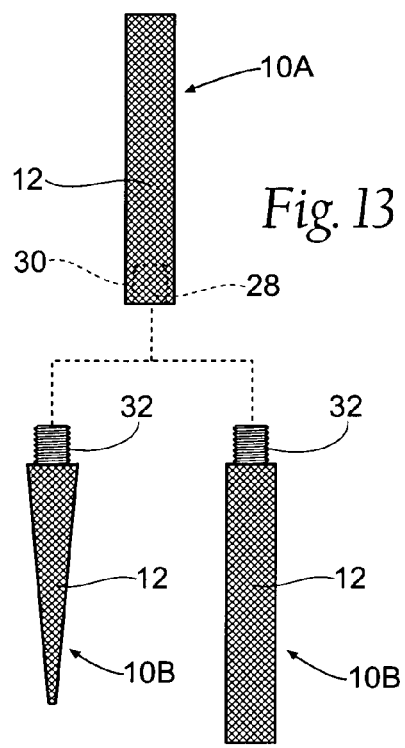
FIG. 13 is an exploded front plan view illustrating the coupling of a pair of bone fixation stems by threaded engagement.

In many cases, it may be desirable to couple a series of devices 10 together, e.g., to provide stabilization over a larger surface area. A series of devices 10 may be coupled together by any suitable means, e.g., by a snap fit engagement or a groove and tab key arrangement. In one embodiment, a series of devices 10 are coupled by threaded engagement. As illustrated in FIG. 13, a first device 10A includes a recess 28 at one end providing a series of internal threads 30. In the illustrated embodiment, the first device 10 is of a cylindrical configuration, but may be of any desired configuration. The internal threads 30 couple with a series of complementary external threads 32 on a second device 10B of a similar or of a different configuration to couple the first and second devices 10A and 10B together.

Figure 14:
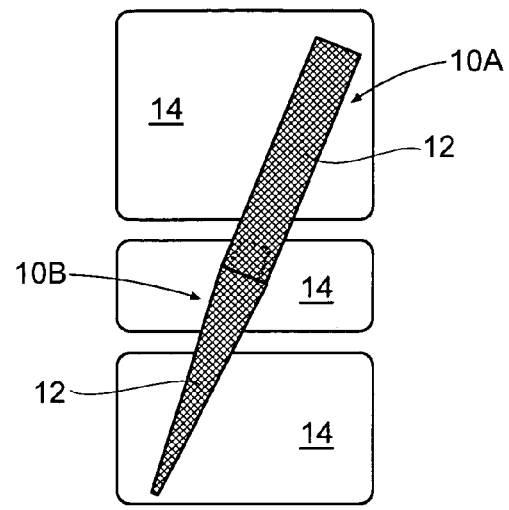
FIG. 14 is a schematic illustrating a pair of bone fixation stems coupled together and inserted into bone across multiple bone segments.

The devices 10A and 10B are desirably coupled together prior to being inserted into the pre-formed bore 26. The series of internal and external threads 30 and 32 provide an interlocking mechanism that permits a series of devices 10 to be stacked and connected to cover a larger area or multiple bone segments 14 (e.g., a bone having multiple fractures) and thereby provides additional stabilization, as seen in FIG. 14.

Figure 15:
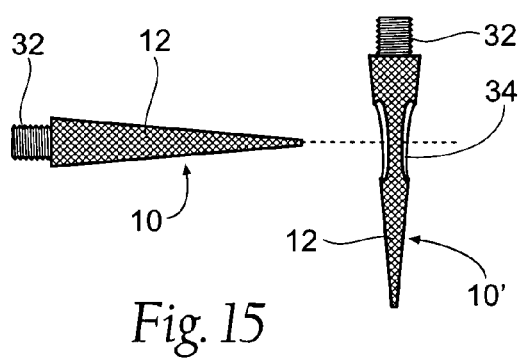
FIG. 15 is a front plan view illustrating passage of a bone fixation stem through a fenestration in another bone fixation stem.

FIG. 15 illustrates another embodiment in which a device 10' includes an opening or fenestration 34 to allow another device 10 to pass through, thereby providing additional stabilization. The fenestration 34 can be sized and configured to permit another device 10 to be passed through the device 10' at virtually any angle. The fenestration 34 can also be sized and configured to limit movement of the second device 10 relative to the first device 10'.

Figure 16:
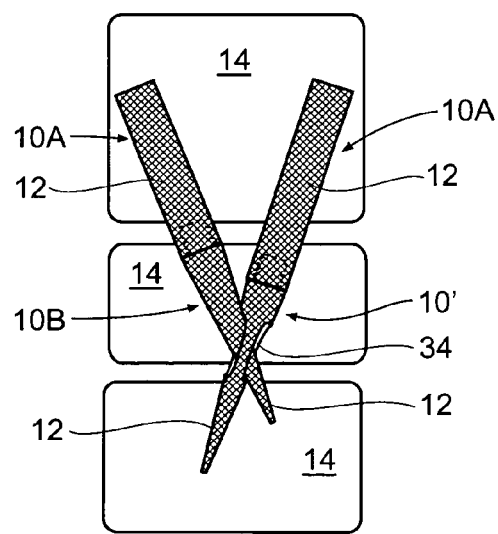
FIG. 16 is a schematic illustrating the placement of a series of bone fixation stems in bone.

In use, and as shown in FIG. 16, the physician taps a first device 10' having a fenestration 34 through the bone segments. A second device 10 is then inserted (e.g., by tapping) through the fenestration 34 of the first device 10' into place.

It is further contemplated that device 10' may also be adapted for coupling with another device 10A (e.g., by a series of external and internal threads), permitting the devices 10' and 10A to be additionally stacked and connected, as also shown in FIG. 16.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method comprising
identifying a bone fracture site comprising a first bone segment, a second bone segment, and a non-bony region comprising a fracture site between the first and second bone segments,
providing a first bone fixation device comprising a first elongated stem structure sized and configured for insertion through the first bone segment, entirely through the fracture site, and at least partially into the second bone segment, and a fenestration in the first elongated stem structure, wherein the fenestration is unthreaded,
providing a second bone fixation device comprising a second elongated stem structure sized and configured for insertion through the first bone segment, entirely through the fracture site, and at least partially into the second bone segment, the second bone fixation device also comprising a non-threaded tapered section, the non-threaded tapered section having a distal portion being sized and configured for passage through the fenestration in the first elongated stem structure, the non-threaded tapered section also having a proximal portion sized and configured such that it is prevented from passing completely through the fenestration in the first elongated stem structure, inserting the first elongated stem structure through the first bone segment, entirely through the fracture site, and at least partially into the second bone segment, and inserting the second elongated stem structure through the first bone segment, entirely through the fracture site, and at least partially into the second bone segment, including passing the distal portion of the non-threaded tapered section of the second elongated stem structure through the fenestration in the first elongated stem structure such that at least a portion of the non-threaded tapered section remains in the fenestration, the fenestration and the non-threaded tapered section cooperating to limit movement of the second elongated stem structure relative to the first elongated stem structure, wherein the first and the second elongated stem structures comprise external surfaces, each of which are non-threaded, wherein the fenestration is sized and configured relative to the non-threaded tapered section to permit the second elongated stem structure to be passed through the first elongated stem structure at a range of angles, thereby providing stabilization of the bone segments from the non-threaded tapered section interlocking with the non-threaded fenestration.

2. The method of claim 1 wherein the first bone fixation device also comprises a non-threaded tapered section.

3. The method of claim 1 wherein at least one of the first and the second bone fixation devices is formed by axially stacking and coupling multiple sections together.

4. The method of claim 1 wherein the insertion step for the second elongated stem structure comprises tapping the second elongated stem structure into place within the fenestration of the first elongated stem structure.

5. The method of claim 1 wherein the second elongated stem structure can be passed through the first elongated stem structure at virtually any angle.

6. The method of claim 1 further comprising the step of using a cannulated drill over a guide pin to form a conical bore through the first bone segment, entirely through the fracture site, and at least partially into the second bone segment prior to inserting the first elongated stem structure therein, wherein the first elongated stem structure has a central lumen extending through it configured to receive the guide pin to assist in the placement of the first elongated stem structure within the bone segments.

7. A method comprising identifying a bone site comprising a first bone segment, a second bone segment, and a non-bony region comprising an interruption between the first and second bone segments, providing a first bone fixation device comprising a first elongated stem structure sized and configured for insertion through the first bone segment, entirely through the interruption, and at least partially into the second bone segment, and a fenestration in the first elongated stem structure, wherein the fenestration is unthreaded, providing a second bone fixation device comprising a second elongated stem structure sized and configured for insertion through the first bone segment, entirely through the interruption, and at least partially into the second bone segment, the second bone fixation device also comprising a non-threaded tapered section, the non-threaded tapered section having a distal portion being sized and configured for passage through the fenestration in the first elongated stem structure, the non-threaded tapered section also having a proximal portion sized and configured such that it is prevented from passing completely through the fenestration in the first elongated stem structure, inserting the first elongated stem structure through the first bone segment, entirely through the interruption, and at least partially into the second bone segment, and inserting the second elongated stem structure through the first bone segment, entirely through the interruption, and at least partially into the second bone segment, including passing the distal portion of the non-threaded tapered section of the second elongated stem structure through the fenestration in the first elongated stem structure such that at least a portion of the non-threaded tapered section remains in the fenestration, the fenestration and the non-threaded tapered section cooperating to limit movement of the second elongated stem structure relative to the first elongated stem structure, wherein the first and the second elongated stem structures comprise external surfaces, each of which are non-threaded, wherein the fenestration is sized and configured relative to the non-threaded tapered section to permit the second elongated stem structure to be passed through the first elongated stem structure at a range of angles, thereby providing stabilization of the bone segments from the non-threaded tapered section interlocking with the non-threaded fenestration.

8. The method of claim 7 wherein the first bone fixation device also comprises a non-threaded tapered section.

9. The method of claim 7 wherein at least one of the first and the second bone fixation devices is formed by axially stacking and coupling multiple sections together.

10. The method of claim 7 wherein the insertion step for the second elongated stem structure comprises tapping the second elongated stem structure into place within the fenestration of the first elongated stem structure.

11. The method of claim 7 wherein the second elongated stem structure can be passed through the first elongated stem structure at virtually any angle.

12. The method of claim 7 further comprising the step of using a cannulated drill over a guide pin to form a conical bore through the first bone segment, entirely through the interruption, and at least partially into the second bone segment prior to inserting the first elongated stem structure therein, wherein the first elongated stem structure has a central lumen extending through it configured to receive the guide pin to assist in the placement of the first elongated stem structure within the bone segments.

13. Apparatus for stabilizing a bone site comprising a first bone segment, a second bone segment, and a non-bony region comprising a fracture site between the first and second bone segments, the apparatus comprising a first bone fixation device comprising a first elongated stem structure sized and configured for insertion through the first bone segment, entirely through the fracture site, and at least partially into the second bone segment, and a fenestration in the first elongated stem structure, wherein the fenestration is unthreaded, and a second bone fixation device comprising a second elongated stem structure sized and configured for insertion through the first bone segment, entirely through the fracture site, and at least partially into the second bone segment, the second bone fixation device also comprising a non-threaded tapered section, the non-threaded tapered section having a distal portion being sized and configured for passage through the fenestration in the first elongated stem structure, the non-threaded tapered section also having a proximal portion sized and configured such that it is prevented from passing completely through the fenestration in the first elongated stem structure, the fenestration and the non-threaded tapered portion being sized and configured such that at least a portion of the non-threaded tapered section remains in the fenestration after the second bone fixation device is inserted, the fenestration and the non-threaded tapered section being sized and configured to limit movement of the second elongated stem structure relative to the first elongated stem structure, wherein the first and the second elongated stem structures comprise external surfaces, each of which are non-threaded, wherein the fenestration is sized and configured relative to the non-threaded tapered section to permit the second elongated stem structure to be passed through the first elongated stem structure at a range of angles, thereby providing stabilization of the bone segments from the non-threaded tapered section interlocking with the non-threaded fenestration.

14. The apparatus of claim 13 wherein the first bone fixation device also comprises a non-threaded tapered section.

15. The apparatus of claim 13 wherein at least one of the first and the second bone fixation devices is formed by axially stacking and coupling multiple sections together.

16. The apparatus of claim 13 wherein the second elongated stem structure can be passed through the first elongated stem structure at virtually any angle.

17. Apparatus for stabilizing a bone site comprising a first bone segment, a second bone segment, and a non-bony region comprising an interruption between the first and second bone segments, the apparatus comprising a first bone fixation device comprising a first elongated stem structure sized and configured for insertion through the first bone segment, entirely through the interruption, and at least partially into the second bone segment, and a fenestration in the first elongated stem structure, wherein the fenestration is unthreaded, and a second bone fixation device comprising a second elongated stem structure sized and configured for insertion through the first bone segment, entirely through the interruption, and at least partially into the second bone segment, the second bone fixation device also comprising a non-threaded tapered section, the non-threaded tapered section having a distal portion being sized and configured for passage through the fenestration in the first elongated stem structure, the non-threaded tapered section also having a proximal portion sized and configured such that it is prevented from passing completely through the fenestration in the first elongated stem structure, the fenestration and the non-threaded tapered portion being sized and configured such that at least a portion of the non-threaded tapered section remains in the fenestration after the second bone fixation device is inserted, the fenestration and the non-threaded tapered section being sized and configured to limit movement of the second elongated stem structure relative to the first elongated stem structure, wherein the first and the second elongated stem structures comprise external surfaces, each of which are non-threaded, wherein the fenestration is sized and configured relative to the non-threaded tapered section to permit the second elongated stem structure to be passed through the first elongated stem structure at a range of angles, thereby providing stabilization of the bone segments from the non-threaded tapered section interlocking with the non-threaded fenestration.

18. The apparatus of claim 17 wherein the first bone fixation device also comprises a non-threaded tapered section.

19. The apparatus of claim 17 wherein at least one of the first and the second bone fixation devices is formed by axially stacking and coupling multiple sections together.

20. The apparatus of claim 17 wherein the second elongated stem structure can be passed through the first elongated stem structure at virtually any angle.

\* \* \* \* \*